(12) United States Patent
Engström et al.

(10) Patent No.: US 8,133,438 B2
(45) Date of Patent: Mar. 13, 2012

(54) FLOW PATHS COMPRISING ONE OR TWO POROUS BEDS

(75) Inventors: Johan Engström, Uppsala (SE); Mats Inganäs, Uppsala (SE); Gunnar Thorsén, Hagersten (SE)

(73) Assignee: Gyros Patent AB, Uppsala (SE)

( * ) Notice: Subject to any disclaimer, the term of this patent is extended or adjusted under 35 U.S.C. 154(b) by 641 days.

(21) Appl. No.: 10/587,428

(22) PCT Filed: Jan. 31, 2005

(86) PCT No.: PCT/SE2005/000114
§ 371 (c)(1),
(2), (4) Date: Apr. 18, 2007

(87) PCT Pub. No.: WO2005/072872
PCT Pub. Date: Aug. 11, 2005

(65) Prior Publication Data

US 2007/0241061 A1    Oct. 18, 2007

Related U.S. Application Data

(60) Provisional application No. 60/540,262, filed on Jan. 29, 2004.

(30) Foreign Application Priority Data

Jan. 29, 2004   (SE) ..................... 0400181

(51) Int. Cl.
*G01N 15/06* (2006.01)
*G01N 1/00* (2006.01)
*B01L 3/00* (2006.01)
(52) U.S. Cl. ....... 422/68.1; 422/239; 422/502; 422/603; 436/175
(58) Field of Classification Search ............ 422/68.1, 422/101, 239, 502, 603; 436/175
See application file for complete search history.

(56) References Cited

U.S. PATENT DOCUMENTS 4,175,073 A   11/1979   Carlsson et al.
(Continued)

FOREIGN PATENT DOCUMENTS

JP   2003-515167   4/2003
(Continued)

OTHER PUBLICATIONS

Japanese Official Action, issued May 11, 2010 (published May 11, 2010) during the prosecution of Japanese Patent Application No. 551006/2006.

(Continued)

*Primary Examiner* — Walter D Griffin
*Assistant Examiner* — Lessanework Seifu
(74) *Attorney, Agent, or Firm* — Fulbright & Jaworski L.L.P.

(57) ABSTRACT

A microfluidic device that comprises a microchannel structure in which there are one, two or more flow paths (101;201a,b;301a,a',b) all of which comprises a porous bed I (104,204,304) that is common for all of the flow paths and exposes an immobilized reactant R that is capable of interacting with a solute S that passes through the bed. The characteristics are that at least one of the flow paths comprises/comprise a second porous bed II (105,205,305) that is placed upstream of porous bed I (104,204,304) and is dummy with respect to interaction with solute S but capable of interacting with a substance DS that is present in a liquid aliquot together with solute S and is capable of disturbing the result of the interaction between solute S and said immobilized reactant R. There is also disclosed a method utilizing the device and variant of the device in which the immobilized R is replaced with a generic affinity ligand $L_I$ and/or porous bed II exposes a generic ligand $L_{II}$ that may be different from $L_I$.

14 Claims, 4 Drawing Sheets

U.S. PATENT DOCUMENTS

| | | | |
|---|---|---|---|
| 4,563,304 | A | 1/1986 | Carlsson et al. |
| 5,887,997 | A | 3/1999 | Watanabe et al. |
| 6,322,682 | B1 | 11/2001 | Arvidsson et al. |
| 6,375,871 | B1 | 4/2002 | Bentsen et al. |
| 6,432,290 | B1 * | 8/2002 | Harrison et al. ............ 204/453 |
| 6,479,299 | B1 | 11/2002 | Parce et al. |
| 6,632,655 | B1 | 10/2003 | Mehta et al. |
| 6,632,656 | B1 * | 10/2003 | Thomas et al. ............ 435/288.5 |
| 6,653,625 | B2 | 11/2003 | Andersson et al. |
| 6,717,136 | B2 | 4/2004 | Andersson et al. |
| 6,812,456 | B2 | 11/2004 | Andersson et al. |
| 6,812,457 | B2 | 11/2004 | Andersson et al. |
| 6,852,851 | B1 | 2/2005 | Kenrick et al. |
| 6,884,395 | B2 | 4/2005 | Andersson et al. |
| 6,919,058 | B2 | 7/2005 | Andersson et al. |
| 6,955,738 | B2 | 10/2005 | Derand et al. |
| 6,967,101 | B1 | 11/2005 | Larsson et al. |
| 6,985,672 | B2 | 1/2006 | Andersson et al. |
| 6,990,290 | B2 | 1/2006 | Andersson et al. |
| 6,992,181 | B2 | 1/2006 | Tooke et al. |
| 2002/0125135 | A1 | 9/2002 | Larsson et al. |
| 2003/0029724 | A1 | 2/2003 | Derand et al. |
| 2003/0053934 | A1 | 3/2003 | Andersson et al. |
| 2003/0054563 | A1 | 3/2003 | Ljungstrom et al. |
| 2003/0066959 | A1 | 4/2003 | Andersson et al. |
| 2003/0129360 | A1 | 7/2003 | Derand et al. |
| 2003/0143114 | A1 | 7/2003 | Andersson et al. |
| 2003/0156763 | A1 | 8/2003 | Soderman |
| 2003/0173650 | A1 | 9/2003 | Larsson et al. |
| 2003/0211012 | A1 | 11/2003 | Bergstrom et al. |
| 2004/0058408 | A1 | 3/2004 | Thomas et al. |
| 2004/0096867 | A1 | 5/2004 | Andersson et al. |
| 2004/0099310 | A1 | 5/2004 | Andersson et al. |
| 2004/0120856 | A1 | 6/2004 | Andersson et al. |
| 2004/0202579 | A1 | 10/2004 | Larsson et al. |
| 2005/0042770 | A1 | 2/2005 | Derand et al. |
| 2005/0141344 | A1 | 6/2005 | Ekstrand et al. |
| 2005/0153431 | A1 | 7/2005 | Andersson et al. |
| 2005/0153432 | A1 | 7/2005 | Andersson et al. |
| 2005/0153433 | A1 | 7/2005 | Andersson et al. |
| 2005/0153434 | A1 | 7/2005 | Andersson et al. |
| 2005/0179901 | A1 | 8/2005 | Ostlin et al. |
| 2005/0186685 | A1 | 8/2005 | Kange et al. |
| 2005/0202471 | A1 | 9/2005 | Tooke et al. |
| 2005/0214442 | A1 | 9/2005 | Larsson et al. |
| 2005/0277195 | A1 | 12/2005 | Holmquist et al. |
| 2005/0279925 | A1 | 12/2005 | Andersson et al. |
| 2006/0002825 | A1 | 1/2006 | Derand et al. |
| 2006/0083496 | A1 | 4/2006 | Andersson et al. |
| 2006/0110294 | A1 | 5/2006 | Hellermark et al. |
| 2006/0148065 | A1 | 7/2006 | Inganaes et al. |

FOREIGN PATENT DOCUMENTS

| | | |
|---|---|---|
| JP | 2003-185663 | 7/2003 |
| WO | WO 91/16966 | 11/1991 |
| WO | WO 98/07019 | 2/1998 |
| WO | WO 98/53311 | 11/1998 |
| WO | WO 99/55827 | 11/1999 |
| WO | WO 99/58245 | 11/1999 |
| WO | WO 00/25921 | 5/2000 |
| WO | WO 00/40750 | 7/2000 |
| WO | WO 00/56808 | 9/2000 |
| WO | WO 00/62042 | 10/2000 |
| WO | WO 00/69560 | 11/2000 |
| WO | WO 00/78455 | 12/2000 |
| WO | WO 00/79285 | 12/2000 |
| WO | WO 01/02737 | 1/2001 |
| WO | WO 01/30500 | 5/2001 |
| WO | WO 01/47637 | 7/2001 |
| WO | WO 01/47638 | 7/2001 |
| WO | WO 01/54810 | 8/2001 |
| WO | WO 01/87486 | 11/2001 |
| WO | WO 01/87487 | 11/2001 |
| WO | WO 02/074438 | 9/2002 |
| WO | WO 02/075312 | 9/2002 |
| WO | WO 02/075775 | 9/2002 |
| WO | WO 02/075776 | 9/2002 |
| WO | WO 03/018198 | 3/2003 |
| WO | WO 03/024598 | 3/2003 |
| WO | 03/072253 A1 | 9/2003 |
| WO | WO 03/093802 | 11/2003 |
| WO | WO 2004/083108 | 9/2004 |
| WO | WO 2004/103890 | 12/2004 |
| WO | WO 2004/106926 | 12/2004 |
| WO | WO 2005/065827 | 7/2005 |
| WO | WO 2005/066066 | 7/2005 |
| WO | WO 2005/072872 | 8/2005 |

OTHER PUBLICATIONS

Office Action issued in Japanese Application No. 2006-551006, mailed Dec. 7, 2011.

Buranda, Tione, Jinman Huang, Victor H. Perez-Luna, Brett Schreyer, Larry A. Sklar and Gabriel P. Lopez; "Biomolecular Recogniation on Well-Characterized Beads Packed in Microfluidic Channels"; Analytical Chemistry; vol. 74, No. 5 (Mar. 1, 2002) pp. 1149-1156.

Piyasena, Menake E., Tione Buranda, Yang Wu, Jinman Huang, Larry A. Sklar, and Gabirel P. Lopez; Near-Simultaneous and Real-Time Detection of Multiple Analytes in Affinity Microcolumns:; Analytical Chemistry, vol. 76, pp. 6266-6273.

U.S. Appl. No. 11/397,401.

U.S. Appl. No. 11/301,165.

* cited by examiner

FLOW PATHS COMPRISING ONE OR TWO POROUS BEDS

CROSS REFERENCE TO RELATED APPLICATIONS

This Application is the National Stage Application of International Application No. PCT/SE2005/000114 filed Jan. 31, 2005 that claims priority to Swedish Application No. 0400181-4 filed Jan. 29, 2004 and U.S. Provisional No. 60/540,262 filed Jan. 29, 2004.

TECHNICAL FIELD

The invention relates to a microfluidic device and a microfluidic process comprising steps that are carried out in a particular kind of flow path(s) (101;201a,b;301a,a',b) of a microchannel structure of the device. The part of the process comprises that a solute S is allowed to interact with a reactant R that is immobilized to a solid phase material. The particular flow path(s) concerned comprises/comprise the solid phase material in the form of a porous bed I (204,204,304) in the flow path(s) (101;201a,b;301a,a',b).

The process comprises for instance:
a) removal including separation of solute S from the liquid, i.e. solute S is retained or degraded by the solid phase, e.g. by affinity to groups on porous bed I, and/or
b) a catalytic reaction, e.g. an enzymatic reaction, with one component of the catalytic system used being the immobilized reactant R, and/or
c) solid phase synthesis.

For variants (a) and (b) the process of the invention is typically part of an analytical assay or protocol in which an uncharacterized aspect of a reactant (=analyte) is characterized/determined, e.g. identity, structural features, amount in absolute or relative terms such as concentration, etc. The term "reactant" comprises analytes and reagents.

The term "solute" refers to a substance that is in truly dissolved form or in suspended form including colloidal form. The term thus includes microorganisms such as bacteria, mould, viruses, bacteriophages etc, and fragments thereof when they are used in suspended forms.

All patents and patent application cited herein are incorporated in their entirety by reference.

BACKGROUND OF THE INVENTION

WO 02075312 (Gyros AB) describes a microfluidic device in which there is a microchannel structure which each comprises a separation unit for removing particulate material from a liquid aliquot. The liquid aliquot contains also a solute that in a subsequent step is a reactant in an affinity based assay.

PCT/SE2004/001424, WO 0147638 (Gyros AB), WO 03098302 (Gyros AB), WO 02075775 (Gyros AB), WO 02075775 (Gyros AB) describes various structures for which it has been suggested with upstream processing of a liquid sample followed by downstream processing of the result of the upstream processing, possibly including a determination step.

U.S. Pat. No. 6,632,655 (Caliper), Piyasena et al (Anal. Chem. 76 (2004) 6266-6273) and Buranda et al (Anal. Chem. 74 (2004) 1149-1156) describe a porous bed that comprises segments. The bed is used in multi-analyte assays.

Many samples, such as biological fluid samples, many times contain disturbing substances that are capable of negatively affecting results of reactions between a solute and a reactant immobilized to a porous bed. This has created problems for us in sandwich assays as outlined in WO 02075312 (Gyros AB) and WO 04083108 (Gyros AB), i.e. with the analyte being equal to solute S above. If a substance is disturbing or not or to what degree will depend on kind of sample, among others. A disturbing substance may be a dissolved compound, an aggregate and/or a particulate material including also various kinds of mal-functioning reagents (see below). For biologically derived samples particulate material may be cell debris and the like, lipids etc. The problem encountered may be linked to type of reactants, e.g. analyte. Membrane associated biological analytes are often accompanied by relatively large amounts of particulate material disturbing an assay. Samples from cells, tissue and body fluids are typically difficult to handle in microfluidic devices. There may be heterophilic antibodies that interact with antibody reagents in an undesired manner in immune assays. Reagent compositions may contain forms that disturb the result of an assay, for instance by creating signal responses that are comparable to or higher than normal back ground responses. Labelled reactants may contain forms that have an abnormal density of labelled groups thereby differing sizely and/or chemically from the normally labelled forms.

BRIEF SUMMARY OF THE INVENTION

The objects of the invention are to provide improvements applicable to microfluidic devices in relation to the above-mentioned problems as well as to other problems. This means methods and microfluidic devices enabling improved detection limits, analyte specificity, diagnostic sensitivity and specificity, precision, dynamic range, recovery etc in analytical assays in which a characteristics of an analyte is determined. The objects of the invention thus aim at a) limits of detection for analytes $\leq 10^{-6}$ M, such as $\leq 10^{-9}$ M or $\leq 10^{-12}$ M or $\leq 10^{-13}$ M or $\leq 10^{-14}$ M or $\leq 10^{-15}$ M or $\leq 10^{-16}$ M, b) dynamic ranges that are two, three, four, five or more orders of magnitude (M), c) precisions (CV) within ±20%, such as within ±10% or within ±5% or within ±3%, d) recoveries $\geq 70\%$ such as $\geq 80\%$ or $\geq 90\%$ or $\geq 95\%$ or around 100% or more. For other process protocols such as of the type indicated under the heading "Technical Field", the objects relate to improved performance with respect to other relevant variables, e.g. number of acceptable experiments/runs of a process per time unit, precision, reproducibility in yield etc.

DETAILED DESCRIPTION OF THE INVENTION

We have realized that these objects can be complied with by
a) providing a solid phase material in the form of a porous bed II (105,205,305) in a flow path (101,201a,301a,a') of a microchannel structure in a position upstream of porous bed I (104,204,304) where porous bed II (105,205,305) is dummy in relation to solute S but not in relation to the disturbing substances, and b) transporting solute S dissolved in a liquid aliquot containing one or more disturbing substances through porous bed II (105,205,305) before the solute and accompanying liquid is transported through porous bed I (104,204,304).

Porous bed II (105,205,305) is dummy in relation to solute S, i.e. solute S is able to pass through the bed unaffected while disturbing substances are neutralized in the bed by interaction with the solid phase material. Neutralization means degraded, captured or otherwise hindered from passing into porous bed I (104,204,304) simultaneously or before solute S. Solute S will thus be allowed to interact with the solid phase material of porous bed I (104,204,304) in the absence of the disturbing substances that have been neutralized in porous bed II (105,205,305).

The first aspect of the invention is a microfluidic device that comprises one, two or more microchannel structures. Each of the microchannel structures comprises one or more flow paths (101;201a,b;301a,a',b) that comprise a common reaction microcavity I (102,202,302) that retains a solid phase material in the form of a common porous bed I (104,204,304). This bed exposes or is intended to expose an immobilized reactant R that is capable of interacting with a solute S that passes through the bed. Common in this context means that all the flow paths pass through the this reaction microcavity I/porous bed I (102,202,302/104,204,304).

The main characteristic feature of the device is that the microchannel structure comprises a second porous bed II (105,205,305) that is placed upstream of porous bed I (104,204,304). Porous bed II (105,205,305) is placed in reaction microcavity II (103,203,303) that may be physically separated from reaction microcavity I (102,202,302) or joined with reaction microcavity II (103,203,303) to form an enlarged reaction microcavity I+II. If the two porous beds I and II are placed in such a reaction microcavity they form a joint porous bed comprising an upstream segment corresponding to porous bed II (105,205,305) and a downstream segment corresponding to porous bed I (104,204,304). In other words the downstream end of the upstream segment is abutted to the upstream end of the downstream segment. This includes that a porous membrane (106) may be placed between the segments in order to secure that the two solid phase materials are not intermixed at their interface. Porous bed II (105,205,305) is dummy with respect to interaction with solute S but not with respect to disturbing substances.

A microcavity, microconduit, or other functional unit is said to be in liquid communicting with another microcavity, microconduit, or other functional unit in the case liquid is intended to be transported from the former to the latter.

Disturbing Substances

A disturbing substance is capable of disturbing the outcome of one or more of the desired interactions taking place in and downstream of porous bed I (104,204,304) in the sense that the substance has a negative impact on the result obtained. For processes in general there are a number of quality parameters (results) that may be adversely affected, e.g. amount of time required for performing a single experiment or run of the same process/method (increasing), productivity measured as number of runs per time unit (decreasing), recovery or loss of one or more of the individual reactants used (decreasing or increasing, respectively), yield of one or more products obtained (decreasing), precision related to product parameters such as yield, purity, etc (increasing), For analytical assay protocols one or more of the following quality parameters may be adversely affected: precision (lowering), limit of detection (increasing), dynamic range (narrowing), analyte sensitivity (lowering), diagnostic sensitivity and specificity (lowering), recovery (lowering), undesired loss of a reactant used (increased), such as of the analyte etc.

A disturbing substance may be in dissolved form and/or in particulate form. Particulate forms include any form that is not a dissolved form. In particulate forms a disturbing substance may exert its adverse effect by clogging porous bed I or other porous beds that may be present downstream of porous bed I. Truly dissolved forms of a disturbing substance have a low risk to clog a porous bed, unless they easily are transformed to particulate forms upstream of or in a bed during the process. Dissolved forms of disturbing substances may exert their disturbing effects:

a) by inherently comprising measurable characteristics that coincide with or otherwise disturb the characteristics utilized for the measurement of the desired product or by participating in reactions that during the process result in an entity comprising such measurable characteristics, and/or b) by interfering with the desired reactions of the process, for instance by neutralizing or otherwise consuming the activity of added reactants (e.g. the analyte and/or one or more of the reagents added), and/or c) by interacting with inner surfaces of the microchannel structure used thereby causing enhanced undesired interaction of one or more of the reactants with inner surfaces (e.g. undesired binding to solid phase material and/or to inner surfaces), and/or d) by transformation to particulate forms thereby causing precipitates including deposits and/or sediments in the microchannel structure (e.g. in the porous bed, the measuring zone and/or elsewhere).

In the context of the invention disturbing substances are primarily considered in liquids in which solute S is a reactant, e.g. an analyte or a reagent. Liquids in this context refer to liquids that are intended to be dispensed unprocessed to the microfluidic device.

Reagent-containing liquids: This kind of liquids is typically man-made. Disturbing substances deriving from solvent and buffer components are thus relatively easy to avoid. The reagent part may be more complicated. An organic reagent, such as a bio-organic reagent, is typically manufactured from more complex materials and often contains disturbing substances (contaminants) that are difficult to remove. There is thus a risk that these substances remain in the liquid to be used. Reagents that have been obtained by derivatization of bio-organic compounds, e.g. exhibiting peptide/amino acid, nucleotide, carbohydrate, and/or lipid structure (including steroid structure), may thus be contaminated with starting material, side products etc. In addition to the reagents used for labelling, a labelled reagent may contain a spectrum of molecular entities that differ with respect to activity and/or to number of labels and/or positions at which the individual labels are attached. A conjugate between two substances A and B may contain a spectrum of molecular entities that varies with respect to activity and/or number of A and/or B, ratio between number of A and number of B and/or positions in A that is attached to B and positions in B that is attached to A. Derivatized reagents that have been obtained by fragmentation may contain a spectrum of fragments varying in activity. Reagents in un-derivatized forms may also contain disturbing contaminants, e.g. if they derive from biological material and/or exhibit at least one structure selected amongst peptide or amino acid, nucleotide, carbohydrate, and/or lipid structure including steroid structure. Both derivatized reagents and reagents in un-derivatized form may contain aggregated reagents, e.g. having a spectrum of molecular weights. Thus, some of the molecules in a reagent composition may increase the limit of detection and/or the sensitivity by possessing a higher tendency than the others to participate in side reactions, such as unspecific binding to porous bed I (104,204, 304) and to inner surfaces of the microchannel structure.

Analyte-containing liquids: This kind of liquids is typically represented by samples that have a significant inter-sample variation with respect to the concentration of analyte and other constituents. An analyte-containing liquid sample typically originates from a complex mixture and thus contains a large number of substances that might disturb an assay carried out according to the invention. Analyte-containing samples thus may derive from the process stream of an industrial or laboratory process or method. The process may be a non-biological process or a biological process in the sense that it utilizes at least some kind of biologically derived material that has been obtained by a chemical or biochemical method, for instance comprising a bio-organic material that exhibits at least one structure selected from peptide or amino acid structure, nucleotide structure, carbohydrate structure and/or lipid structure including hormone structure. An important source of sample is biological fluids (i.e. liquids), such as blood and various fractions thereof such as plasma and serum, lymph, urine, cerebrospinal fluid (CSF), lachrymal fluid, saliva, intestinal fluid, gastric fluid, regurgitated fluid, sweat, cell homogenates, tissue supernatants, artificial biological fluids etc. The term "biological fluid" also contemplates fractions deriving from one or more of these fluids and comprising a bio-organic compound, typically exhibiting any of the biochemical structures given in this specification. Artificial biological fluids contemplate liquids to which one or more bio-organic molecule of the kinds described herein have been added.

There are three main kinds of disturbing substances that may be present in the analyte-containing liquids discussed above (endogenous substances):

A) Particulate materials as described above. For blood derived samples the term particulate material includes blood corpuscles, such as thrombocytes, blood cells, such as erythrocytes and lymph cells, and fragments of these corpuscles, coagulation products such as fibrin, blood clots and fragments thereof, and other blood precipitation products. For biological fluids in general, particulate material may be cell-related and include cells and their fragments, tissue fragment, neutral and/or ionic lipids in un-dissolved form etc.

B) Substances that form precipitates, sediments or deposits as described above.

C) Substances that interact in an undesired manner with a reagent used in the process so that an entity is formed comprising measurable characteristics that are indistinguishable from the characteristics to be measured. The reagent may be the immobilized reagent R, or a reagent in dissolved form, such as reagent in labelled and/or conjugate form. Heterophilic antibodies are important in this context, i.e. sample endogenous antibodies that are reactive with antibody reagents that expose antigenic determinants that are capable of binding to endogenous antibodies of the sample. Endogenous carrier proteins for the analyte may also be important, in particular if the analyte is of low molecular weight (e.g. $\leq$10,000 dalton, such as $\leq$5,000 daltons) and/or if its free form is to be determined. Other examples are endogenous constituents that have the same measurable characteristics as a label used. An endogenous enzyme may disturb the measurement if the label used on a reactant utilizes the same substrate as the endogenous enzyme, for instance.

D) Bulk protein, such as albumin, gamma-globulin including particularly IgG and IgA, antitrypsin, and haptoglobulin may disturb and therefore worth removing even if they are not acting as a carrier protein according to (C).

Solid Phase Materials in Porous Bed I and II.

The solid phase material in porous bed I (104,204,304) and porous bed II (105,205,305) may be of the same or different kinds. Thus the downstream bed (104,204,304) may be a porous monolithic plug and the upstream bed (105,205,305) a packed bed of particles, or the other way round, or both beds may be porous monoliths or porous beds of packed particles. The solid phase material in the two beds may also differ with respect to one or more of base material, particle size (and particle size distribution), porosity, coatings, hydrophilicity/hydrophobicity, swellability, elasticity, rigidity etc.

Suitable particles are spherical or spheroid (beaded) or non-spherical. Suitable mean diameters for particles used as solid phase material are typically found in the interval of 1-100 μm with preference for mean diameters that are $\geq$5 μm, such as $\geq$10 μm or $\geq$15 μm and/or $\leq$50 μm. Also smaller particles can be used, for instance with mean diameters down to 0.1 μm. The outlet of a reaction microcavity and the particles used should match each other so that the particles can be retained in the reaction microcavity. Diameters refer to the "hydrodynamic" diameters. Particle preparations may be monodisperse (monosized) or polydispersed (polysized). Particles may be either porous or non-porous. The term monosized/polysized and porous/non/porous have the same meaning as in WO 02075312 (Gyros AB).

The base material of a solid phase may be made of inorganic and/or organic material. Typical inorganic materials comprise glass and typical organic materials comprise organic polymers. Polymeric materials comprise inorganic polymers, such as glass, and organic polymers that may be of synthetic or biological origin (biopolymers). The term biopolymer includes semi-synthetic polymers in which there is a polymer backbone derived from a native biopolymer. Typical synthetic organic polymers are cross-linked and are often obtained by the polymerisation of monomers comprising polymerisable carbon-carbon double bonds. Examples of suitable monomers are hydroxy alkyl acrylates and corresponding methacrylates, acryl amides and methacrylamides, vinyl and styryl ethers, alkene substituted polyhydroxy polymers, styrene, etc. Typical biopolymers may or may not be cross-linked. In most cases they exhibit a carbohydrate structure, e.g. agarose, dextran, starch etc.

The term "hydrophilic" in the context of a porous bed contemplates ability to absorb water when contacted with water. The expression also means that the inner surfaces of the bed that are in contact with a liquid during the absorption shall expose a plurality of polar functional groups which each has a heteroatom selected amongst oxygen and nitrogen, for instance. Appropriate functional groups can be selected amongst hydroxy groups, ethylene oxide groups (—X—[—$CH_2CH_2O$—]$_n$ where n is an integer >1 and X is nitrogen or oxygen), amino groups, amide groups, ester groups, carboxy groups, sulphone groups etc, with preference for those groups that are essentially uncharged independent of pH, for instance within the interval of 2-12. For solid phase materials in particle form this means that at least the outer surfaces of the particles have to exhibit polar functional groups.

If the base material of a solid phase material is hydrophobic or not sufficiently hydrophilic, e.g. is based on a styrene or polyolefin (co)polymer, the surfaces that are to be in contact with an aqueous liquid may be hydrophilized. Typical protocols comprise that the solid phase material is coated with a compound or mixture of compounds exhibiting polar functional groups of the same type as discussed above, Solid phase material in porous bed I (104,204,304) and porous bed II (105,205,305) is in principle selected amongst the same solid phase material as for $AC_S$ in WO 04083108 (Gyros AB). Selection criteria or features based on the presence of bed-preserving agents may or may not be applied. An additional criterion for material in porous bed II (104,204, 304) is that size exclusion materials in certain variants may be beneficial.

Porous bed II (105,205,305) may be considered as a filter for a liquid containing both a disturbing substance and solute S. In the case the disturbing substance is a particulate material it will be mechanically collected at or in the upper end of porous bed II (105,205,305). If the disturbing substance is in dissolved form there are two main choices for preventing the reactant to reach porous bed I (104,204,304) before or simultaneously with solute S: a) provide the solid phase material with an immobilized reactant $R_{DS}$ that is capable of neutralizing the disturbing substance as indicted elsewhere in this specification, and/or b) provide the solid phase material in the form of a size exclusion material that delay the disturbing substance but not solute S.

It follows that properly selected size exclusion solid phase material may have a number of advantages since they, with the appropriate immobilized $R_{DS}$, will be active in neutralizing disturbing substances in the form of a) particulate material, b) compounds that are reactive with $R_{DS}$, and c) dissolved compounds that have smaller sizes than solute S. Preferred size exclusion material or media are liquid chromatography size exclusion material including gel filtration material. In this context "a smaller size" typically refers to a lower molecular weight and/or a smaller hydrodynamic size. Dissolved disturbing substances of low molecular weight may be found amongst substances that have molecular weights $\leq 100,000$ daltons, such as $\leq 50,000$ daltons or $\leq 10,000$ daltons or $\leq 7,000$ daltons. The terms "smaller size" and "molecular weight" given above refer to measurements done with chromatographic size exclusion material.

It is believed that proper size exlusion media are selected amongst solid phase materials that have Kav-values <0.5, such as <0.4 or <0.1, for a reactant (solute S) that is to pass through porous bed II. Suitable size exclusion media should also have a Kav-value within the range of 0.1-0.95, typically within 0.40-0.95, if the goal is to delay small or low molecular weight disturbing substances or compounds that are not allowed to reach porous bed I before or simultaneously with solute S. For a definition of Kav see L. Hagel in "Protein Purification, Principles, High Resolution, and Applications", J-C Janson and L Rydén (Eds), VCH Publishers Inc. New York, 1989, p. 99.

The selection of immobilized reactant $R_{DS}$ is done according to well known principles and depends on kind of disturbing substance. $R_{DS}$ may thus be a) chemical reactant capturing the disturbing substance by covalent bonds to porous bed II (105,205,305) or otherwise making the substance harmless to the process, b) a component of a catalytic system that converts the substance to a harmless product, c) an affinity counterpart ($AC_{DS}$) to the disturbing substance. Heterophilic antibodies of analyte-containing samples may for instance be captured to porous bed II (105,205,305) according to (c) in the case $AC_{DS}$ is an immunoglobulin preparation of irrelevant antibody activity (cold Ig) but exposing antigenic determinants reactive with antibody-active parts of the heterophilic antibodies. The solid phase material of porous bed II (105, 205,305) may be a HIC-media, i.e. a hydrophilic separation medium comprising hydrophobic groups ($=AC_{DS}$) that potentially will interact and neutralize disturbing substances exposing hydrophobic groups such as lipoid-like substances and/or reagent fractions that are more hydrophobic than other reagent fractions.

Immobilization of $R_{DS}$ may take place by techniques well-know in the field as discussed for the immobilized reagent R. The use of generic immobilizing affinity pairs (binder $B_{DS}$ and ligand $L_{DS}$), such as streptavidin and biotin, respectively, can be envisaged to be particularly useful.

Further information about selection of immobilized $R_{DS}$, such as $AC_{DS}$, and immobilization techniques are found in WO 04083108 (Gyros AB) and in the discussion below about $AC_S$.

It can be envisaged that an immobilized amphiphilic macromolecular substance that typically is capable of forming micelles in water potentially may be particularly useful as an immobilized $R_{DS}$ for removing disturbing effects from derivatized reagent molecules. Suitable such macromolecular substances are selected macromolecular substances exhibiting peptide structure, such as milk proteins e.g. caseins with preference for beta-casein. Suitable such substances may also be found amongst synthetic amphiphilic macromolecular substances such as tri block polymers comprising a central block of a hydrophobic polymer chain, e.g. a polypropylene oxide chain and end blocks of hydrophilic polymer chains, e.g. a polyethylene oxide. See further SE application 05001318 and corresponding US regular application "Protecting agent" filed the 20 Jan. 2005. It is believed that the most significant improved effects for this kind of $R_{DS}/AC_{DS}$ may occur with respect to downward extensions of dynamic ranges and limits of detection, and increased sensitivity in the lower part of a dynamic range. It is believed that this variant may be particular valuable for derivatized reagents, e.g. reagents in which hydrophobic groups, such as hydrophobic labels, have been introduced.

The solid phase material of porous bed I contains an immobilized reactant R that is capable of participating in organic, inorganic, biochemical interactions etc. Depending on the circumstances and the kind of reactant and solute S the interaction may be part of a a) separation, b) a catalytic reaction, c) an affinity reaction, d) a solid phase synthesis, and e) etc.

Immobilized reactant R may in any of a)-e) be an affinity counterpart $AC_S$ to solute S, i.e. capable of forming an affinity complex $AC_S$-S with solute S. Affinity bonds typically are based on: (a) electrostatic interactions, (b) hydrophobic interactions, (c) electron-donor acceptor interactions, and/or (d) bioaffinity binding.

Each of the affinity counterpart $AC_S$ and solute S is thus a bioaffinity reactant/member of a bioaffinity pair. Typical bioaffinity pairs are a) antigen/hapten and an antibody, b) complementary nucleic acids, c) immunoglobulin-binding protein and immunoglobulin (for instance IgG or an Fc-part thereof and protein A or G), d) lectin and the corresponding carbohydrate, e) biotin and (strept)avidin/neutravidin, e) components of an enzymatic system (enzyme-substrate, enzyme-cofactor, enzyme-inhibitor etc), f) an IMAC group and an amino acid sequence containing histidyl and/or cysteinyl and/or phosphorylated residues (i.e. an IMAC motif), etc. Antibody includes antigen binding fragments and mimetics of antibodies. The term "bioaffinity pair" includes also affinity pairs in which one or both of the members are synthetic, for instance mimicking one or both of the members of a native bioaffinity pair. The term IMAC stands for an immobilized metal chelate.

The term "affinity reactant" also includes that solute S or $AC_S$ may be a reactant that is capable of reversible covalent binding, for instance by disulfide formation. This kind of reactants typically exhibits a HS— or a —S—SO$_n$— group (n=0, 1 or 2, free valences bind to carbon). See U.S. Pat. No. 5,887,997 (Batista), U.S. Pat. Nos. 4,175,073 (Axén et al), and 4,563,304 (Axén et al). The immobilized reactant R may be a catalytic system as such or a component of a catalytic system. Components of catalytic systems are catalysts, cocatalysts, cofactors, substrates or cosubstrates, inhibitors, promotors etc. For enzymatic systems the corresponding components are enzymes, cocatalysts, cofactors, coenzymes, substrates, cosubstrates etc. The term "catalytic system" also includes linked catalytic systems, for instance a series of systems in which the product of the first system is the substrate of the second catalytic system etc and whole biological cells or part of such cells.

An immobilized affinity reactant (R, such as $AC_S$) should be selected to have the appropriate selectivity and specificity for interacting with solute S in relation to an intended application. General methods and criteria for the proper selection of reactant R are well known in the field.

The linkage to the solid phase material may be via covalent bonds, affinity bonds (for instance biospecific affinity bonds), physical adsorption etc. The techniques for immobilization are commonly known in the field.

Immobilization via affinity bonds may utilize a generic immobilizing affinity pair in which one of the members (immobilized ligand or L) is firmly attached to the solid phase material, for instance covalently. The other member (immobilizing binder, B) of the pair is used as a conjugate (immobilizing conjugate) comprising binder B and reactant (R e.g. $AC_S$). Examples of immobilizing affinity pairs are a) streptavidin/avidin/neutravidin and a biotinylated reactant (or vice versa), b) antibody and haptenylated reactant (or vice versa), c) an IMAC group and an amino acid sequence containing histidyl and/or cysteinyl and/or phosphorylated residues (i.e. an IMAC motif) linked to a reactant/solute S, etc. An immobilizing binding pair to be used in the invention is generic in the sense that the utilized affinity binding is irrelevant to subsequent affinity reactions.

The term "conjugate" primarily refers to covalent conjugates, such as chemical conjugates and recombinantly produced conjugates (where both the moieties have peptide structure). The term also includes so-called native conjugates, i.e. affinity reactants exhibiting two binding sites that are spaced apart from each other, with affinity directed towards two different molecular entities, for instance a native antibody that comprises species and class-specific determinants on one side of the molecule and antigen/hapten-binding sites on another side.

Preferred immobilizing affinity pairs (L and B) typically have affinity constants ($K_{L-B}$=[L][B]/[L-B]) that are at most equal to or $\leq 10$ times or $10^2$ times or $\leq 10^3$ times larger than the corresponding affinity constant for streptavidin and biotin. This typically will mean affinity constants that roughly are $\leq 10^{-13}$ mole/l, $\leq 10^{-12}$ mole/l, $\leq 10^{-11}$ mole/l and $\leq 10^{-10}$ mole/l, respectively. The preference is to select L and B amongst biotin-binding compounds and streptavidin-binding compounds, respectively, or vice versa, including as biotin-binding compounds anti-biotins such as avidin, streptavidin, neutravidin and other recombinatly chemically varied forms of avidin, streptavidin and neutravidin, anti-biotin antibodies.

The affinity constants discussed above refer to values obtained by a biosensor (surface plasmon resonance) from Biacore (Uppsala, Sweden), i.e. with the affinity reactant ($AC_S$ and L) immobilized to a dextran-coated gold surface.

At least one member of an affinity pair, in particular a bioaffinity pair, to be used in the present invention may exhibit a structure selected amongst: a) amino acid structure including peptide structure such as poly and oligo peptide structure, b) carbohydrate structure, c) nucleotide structure including nucleic acid structure, d) lipid structure such as steroid structure, triglyceride structure etc. The term affinity pair in this context refers to the immobilizing affinity pair (L and B), the affinity reactant and the solute ($AC_S$ and S) and other affinity pairs that may be used for instance for immobilizing $R_{DS}$.

Flow Paths and Reaction Microcavities/Porous Beds

A typical microchannel structure according to the invention comprises one, two, three or more flow paths (101;201a,b;301a,a',b) which each have a section (108,208) that is common to all of the flow paths. In this common section (108,208) there is a reaction microcavity I (102,203,303) containing a porous bed I (104,204,304) that also is common for all of the flow paths (101;201a,b;301a,a',b). Each flow path is used for transporting liquid through porous bed I (104,204,304). See FIGS. 1-3. Upstream of the common section there is an upstream reaction microcavity (102,202,202) containing a porous bed II (105,205,305) in at least one of the flow paths (101;201a;301a,a').

Porous bed I (104,204,304) exhibits a reactant R which is capable of interacting with solute S that is present in a liquid passing through the bed (104,204,304). Porous bed II (105) may or may not exhibit a reactant ($R_{DS}$) that is capable of interacting with a disturbing substance DS that is present in a liquid passing through the bed, for instance in a liquid containing solute S. Interaction between porous bed II (105,205, 305) and the disturbing substance may also occur by size exclusion if the disturbing substance has a smaller size than solute S and the solid phase material of porous bed II (105, 205,305) is appropriately selected.

Porous bed I (104,204,304) and/or porous bed II (105,205, 305) may alternatively exhibit a generic ligand of a generic immobilizing affinity pair. In this variant the generic ligand may have the same binding specificity in at least two porous beds of a microchannel structure, e.g. porous beds I and II (104,204,304 and 105,205,305) in the same flow path may have essentially identical generic ligands (same ligands). Thus, both porous bed I (104,204,304) and porous bed II (105,205,305) in the same flow path (101;201a;301a,a') may have biotin as a generic ligand (or an anti-biotin). Alternatively a generic ligand may have different binding specificity in porous beds I and II (104,204,304 and 105,205,305) in the same flow path. Thus, porous bed I (104,204,304) may have biotin and porous bed II (105,205,305) an anti-biotin or vice versa as generic ligands L in the same flow path (101;201a; 301a,a').

A reaction microcavity comprising porous bed I or II (104, 204,304 and 105,205,305, respectively) is defined as the volume occupied by the bed. These reaction microcavities may like microcavities in general be a straight or bent microconduit that may or may not be continuously widening and/or narrowing. A microcavity that is located at the same position and/or function in one microchannel structure typically has essentially the same shape and/or size as the corresponding microcavity in another microchannel structure. As for reaction microcavities in general, a microcavity containing porous bed I or II (104,204,304 and 105,205,305) has at least one cross-sectional dimension that is $\leq 1,000$ µm, such as $\leq 500$ µm or $\leq 200$ µm (depth and/or width). The smallest cross-sectional dimension is typically $\geq 5$ µm such as $\geq 25$ µm or $\geq 50$ µm. The total volume of a reaction microcavity is typically in the nl-range, such as ≦5,000 nl, such as 1,000 nl or ≦500 nl ≦100 nl or ≦50 nl or ≦25 nl.

Figure 1A:
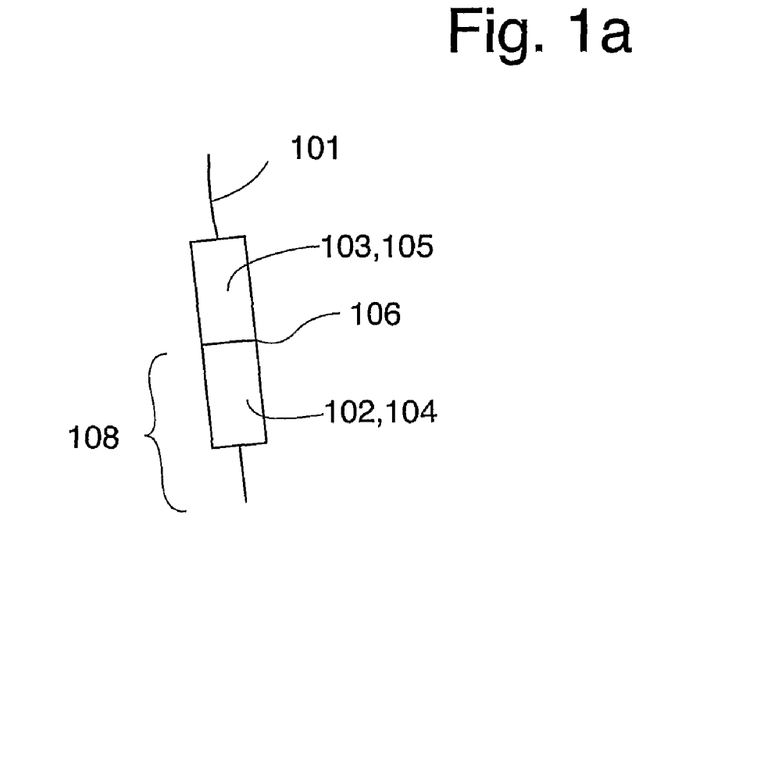
FIGS. 1a-b illustrate two variants having two different porous beds linked in series in a common flow path.

FIG. 1a illustrates variants in which there is at least one flow path (101) with one single reaction microcavity (102+103) for both porous bed I (104) and porous bed II (105). The downstream end of the upstream bed (105) is abutted to the upstream end of the downstream bed (104), possibly including a porous membrane (106) between the beds (104,105).

Figure 1B:
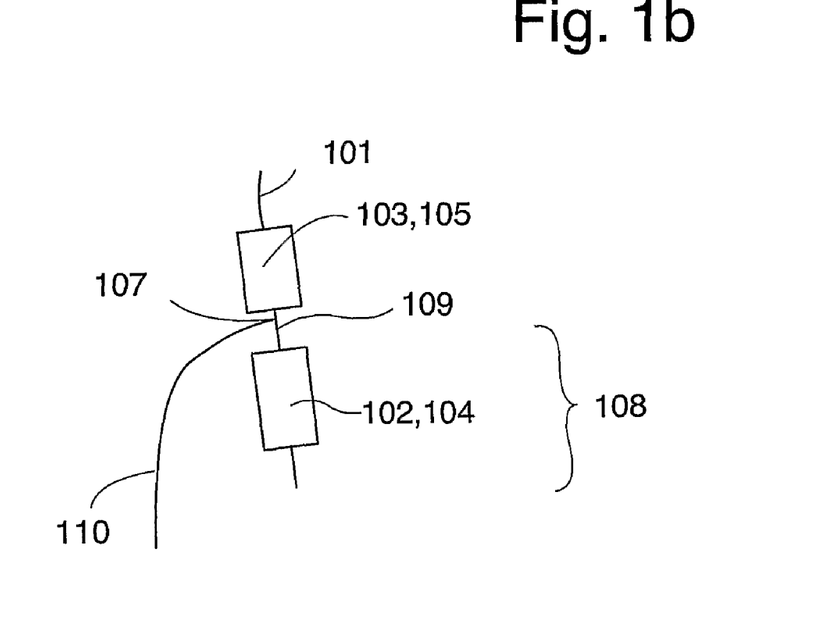

FIG. 1b illustrates variants in which there is at least one flow path (101) with two separate microcavities I and II (102 and 103, respectively)—one for porous bed I (104) and one for porous bed II (105). As discussed in more detail for FIG. 2 there may be a liquid router function (107) between the two reaction microcavities (102 and 103). This router (107) is able to guide liquid into either a micrconduit (109) leading to porous bed I (104) or a microconduit (110) that permits liquid to exit the flow path (101)

Figure 2:
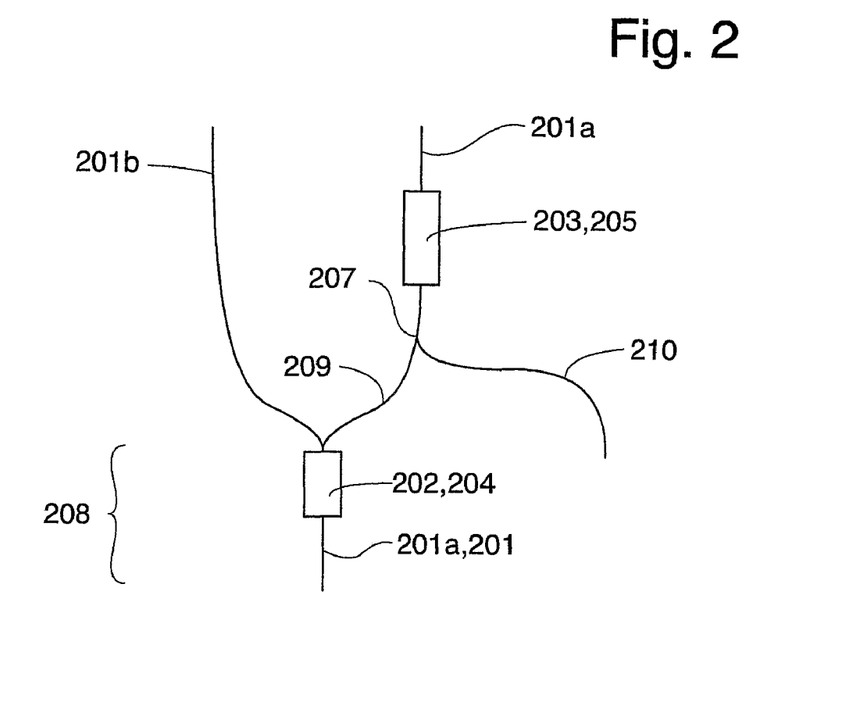
FIG. 2 illustrates a variant with two flow paths that have a common porous bed. One of the flow paths has a second porous bed upstream of the common porous bed.

FIG. 2 illustrates variants in which there are at least two kinds of flow paths (201a and 201b). One of them comprises flow paths (201a) in which both porous beds I and II (204 and 205) are present as described above. The other ones comprise flow paths (201b) that are devoid of porous bed II. There may be a liquid router function (207) between the reaction microcavities/beds (202/204;203/205). This function will permit switching liquid to either of the two microconduits A and B (209 and 210, respectively) and make it possible to prevent a liquid that is intended to interact only with porous bed II (205) from passing through porous bed I (204). The liquid router function (207) has a valve function that is mechanical or is based on surface tension. If centrifugal force is used, the routing function may be as described in PCT/SE2004/001424 (Gyros AB). This liquid router function may be advantageous in the case porous bed II (205) initially contains a generic ligand to which one immobilizes reactant $R_{DS}$ in the form of a conjugate containing a generic affinity counterpart (binder) to the generic ligand. Immobilization typically takes place by transporting the liquid containing the conjugate through porous bed II (205) and out through exit microconduit B (210). In the case porous bed I (204) exhibits a generic ligand, the immobilized reactant R is introduced by passing reactant R in the form of a conjugate with a generic counterpart to this ligand (generic binder) via the flow path (201b) through porous bed I (204) i.e. via a flow path that is devoid of porous bed II (205). When performing the actual method the liquid that contains a reactant together with the disturbing substance is passed through bed II (205) and via microconduit A (209) through porous bed I (204). Other liquids may preferably be introduced via flow path (201b) in which there is no porous bed II.

Figure 3:
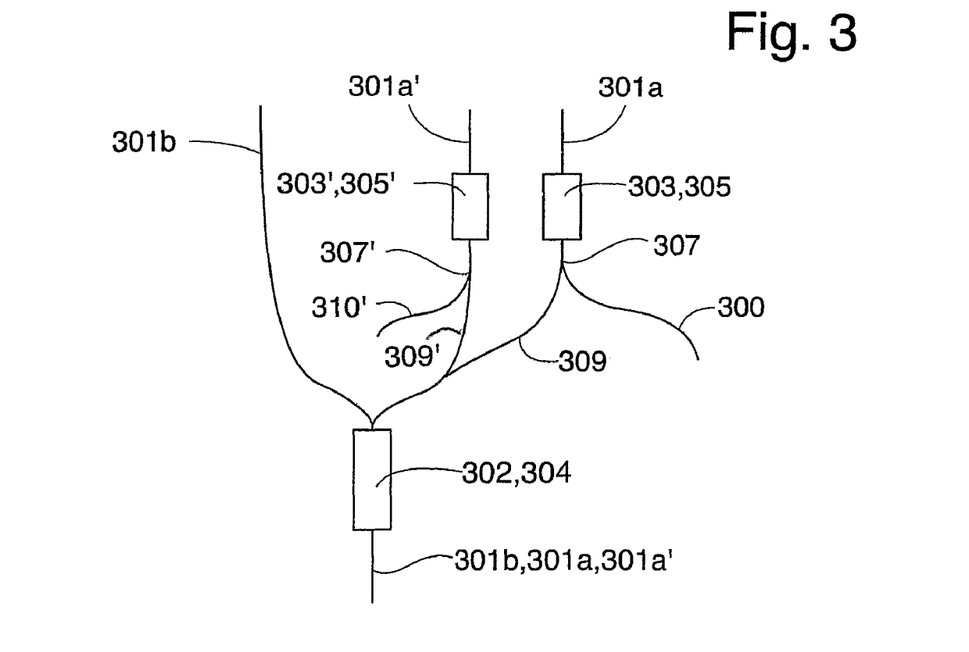
FIG. 3 illustrates a variant with three flow paths that have a common porous bed and one additional porous bed in two out of the three flow paths.

FIG. 3 illustrates another variant in which there are at least two kinds of flow paths (301a,301a' and 301b). One kind comprises flow paths (301a,301a') in which both porous beds I and II (304 and 305) are present. Another kind comprises a flow path (301b) only containing porous bed I (304) that is common for all the flow paths (301a,301a' and 301b). In each flow path (301a,301a') there may be a liquid router (307,307') between porous bed II (305,305') and porous bed I (304,304') with a microconduit A (309) leading to porous bed I, and an exit microconduit B (310). Porous bed II (305) in one or more of the flow paths (301a) containing porous bed II may be different from porous bed II (305') in one or more of remaining ones of the flow paths (301a') containing porous bed II, or essentially identical. The difference may relate to kind of matrix, immobilized reactant ($R_{DS}$) interacting with a disturbing substance, generic ligand, etc. This variant is particularly useful if one liquid contains a first disturbing substance and the other liquid a second different disturbing substance that can not be neutralized by the use of the same solid phase material, for instance the same immobilized reactant $R_{DS}$.

This general outline of microchannel structures that can be used in the present invention can be further illustrated by FIG. 4c in WO 02074438 (Gyros AB), FIG. 1 of WO 04083108 (Gyros AB), and FIG. 2 in PCT/SE2004/001424 (Gyros AB). The structure used in experiment 1 and 2 in this specification was according to FIG. 1 of WO 04083108 (Gyros AB).

The flow paths described above only represent a part of a microchannel structure. In addition there may be one, two, three or more functional units selected among: a) inlet arrangement comprising for instance an inlet port/inlet opening, possibly together with a volume-metering unit, b) further microconduits for liquid transport, c) one or more other reaction microcavities, e.g. for performing homogeneous reactions; d) mixing microcavity; e) unit for separating particulate matters from liquids (may be present in the inlet arrangement), f) unit for separating dissolved or suspended components in the sample from each other, for instance by capillary electrophoresis, chromatography and the like; g) detection microcavity; h) waste conduit/microcavity; i) valve; j) vent to ambient atmosphere; etc. A functional part may have more than one functionality, e.g. a reaction microcavity containing a porous bed I (104,204,304) and a detection microcavity containing porous bed I (104,204,304) may coincide. Various kinds of functional units in microfluidic devices have been described by Gyros AB/Amersham Pharmacia Biotech AB: WO 9955827, WO 9958245, WO 02074438, WO 0275312, WO 03024598, WO 03018198 and by Tecan/Gamera Biosciences: WO 0187487, WO 0187486, WO 0079285, WO 0078455, WO 0069560, WO 9807019, WO 9853311.

Many of these functional units may be present in a microchannel structure used in the invention, for instance upstream of porous bed II (105,205,305), between porous beds II and I (105,205,305 and 104,204,304), and/or downstream of porous bed I (104,204,304) in order to further process liquid aliquots transported in a flow path/microchannel structure. A microchannel structure may also contain additional porous beds upstream or downstream of the porous beds utilised according to main characteristics of the invention. Additional pairs of porous beds I and II in a microchannel structure may define sets of flow paths that are separate from the flow paths (101;201a,b;301a,a',b).

As discussed above a reaction microcavity intended for a porous bed may be connected to one or more inlet arrangements (upstream direction), each of which comprises an inlet port and at least one volume-metering unit. In one advantageous variant, there is one separate inlet arrangement per microchannel structure and reaction microcavity intended to contain the solid phase material. In another advantageous variant, the inlet arrangement is common to all or a subset of microchannel structures (and thus also to a subset of reaction microcavities). This kind of common inlet arrangement typically comprises a common inlet port and a distribution manifold with one volume-metering unit for each microchannel structure/reaction microcavity of the subset. In both variants, each of the volume-metering units in turn is communicating with downstream parts of a microchannel structure and/or a downstream reaction microcavity. Microchannel structures linked together by a common inlet arrangement and/or common distribution manifold define a group of microchannel structures of a device.

Typical inlet arrangements have been presented in WO 0274438 (Gyros AB), WO 0275312 (Gyros AB), WO 0275775 (Gyros AB) and WO 0275776 (Gyros AB).

The microfluidic device may also comprise other common microchannels/microconduits connecting different microchannel structures. Common channels including their various parts such as inlet ports, outlet ports, vents, etc., are considered part of each of the microchannel structures they are communicating with.

Other Features of a Microfluidic Device

A microfluidic device is a device that comprises a microchannel structure in which one or more liquid aliquots in the µl-range, typically in the nanolitre (nl) range, containing various kinds of reactants, such as analytes and reagents, products, samples, buffers and/or the like are processed. A liquid aliquot in the µl-range have a volume $\leq$1,000 µl, such as $\leq$100 µl or $\leq$10 µl and includes the nl-range that has an upper end of 5,000 nl but in most cases relates to volumes $\leq$1,000 nl, such as $\leq$500 nl or $\leq$100 nl. The nl-range includes the picolitre (pl) range. A microchannel structure comprises one or more cavities and/or conduits that have a cross-sectional dimension that is $\leq 10^3$ µm, preferably $\leq 5 \times 10^2$ µm, such as $\leq 10^2$ µm.

A microfludic device preferably contains a plurality of microchannel structures/device intended to contain the solid phase according to the invention. Plurality in this context means two, three or more microchannel structures and typically is $\geq$10, e.g. $\geq$25 or $\geq$90 or $\geq$180 or $\geq$270 or $\geq$360. As discussed above the microcannel structures of a device may be divided into groups, each of which may be defined by the size and/or shape of the reaction microcavity, by a common microchannel, such as a common inlet arrangement or manifold etc. Each such group typically comprises from 3-15 or 3-25 or 3-50 microchannel structures.

Different principles may be utilized for transporting aliquots of liquid within the microfluidic device/microchannel structures between two or more of the functional parts described above. Inertia force may be used, for instance by spinning the disc as discussed below. Other favourable forces are capillary forces, electrokinetic forces, non-electrokinetic forces such as capillary forces, hydrostatic pressure etc.

The microfluidic device typically is in the form of a disc. The preferred formats have an axis of symmetry ($C_n$) that is perpendicular to the disc plane, where n is an integer $\geq$2, 3, 4, 5 or more, preferably $\infty$ ($C_\infty$). In other words the disc may be rectangular, such as squaric, and other polygonal forms but is preferably circular. Once a proper disc format has been established, centrifugal force may be used for driving liquid flow by spinning the device around a spin axis. The spin axis may be perpendicular or parallel to the disc plane. In preferred variants the spin axis coincides with an axis of symmetry.

For preferred centrifugal-based variants, each microchannel structure comprises one upstream section that is at a shorter radial distance than a downstream section relative to a spin axis. A reaction microcavity containing porous bed I and/or II is then at a radial position that is intermediary to the radial positions of the two sections.

The preferred devices are typically disc-shaped with sizes and forms similar to the conventional CD-format, e.g. sizes that are in the interval from 10% up to 300% of the conventional CD-radii.

Microchannels/microcavities of a microfluidic devices may be manufactured from an essentially planar substrate surface that exhibits the channels/cavities in uncovered form that by covering the surface with another essentially planar substrate (lid). See WO 9116966 (Pharmacia Biotech AB) and WO 0154810 (Gyros AB). Both substrates are preferably fabricated from plastic material, e.g. plastic polymeric material.

The fouling activity and hydrophilicity of inner surfaces should be adapted to the process to be carried out in the device. See for instance WO 0147637 (Gyros AB).

The terms "wettable" (hydrophilic) and "non-wettable" (hydrophobic) contemplate that a surface has a water contact angle $\leq$90° or $\geq$90°, respectively. In order to facilitate efficient transport of a liquid between different functional parts, inner surfaces of the individual parts of a microchannel structure should primarily be wettable, preferably with a contact angle $\leq$60° such as $\leq$50° or $\leq$40° or $\leq$30° or $\leq$20°. These wettability values apply for at least one, two, three or four of the inner walls of a microconduit. In the case one or more of the inner walls have a higher water contact angle this can be compensated for by a lower water contact angle for the remaining inner wallS. The wettability, in particular in inlet arrangements should be adapted such that an aqueous liquid will be able to fill up an intended microcavity by capillarity (self suction) once the liquid has started to enter the cavity. A wettable surface of an inner wall of a microchannel structure may comprise one or more local hydrophobic surface breaks in a hydrophilic inner side-wall, for instance for introducing a passive valve, an anti-wicking means, a vent solely function as a vent to ambient atmosphere etc. See for instance WO 9958245 (Gyros AB) and WO 0274438 (Gyros AB).

Contact angles refer to values at the temperature of use, typically +25° C., are static and can be measured by the method illustrated in WO 0056808 (Gyros AB) and WO 0147637 (Gyros AB).

Methods Utilizing the Microfluidic Device

The second aspect of the invention is a method for carrying out a microfluidic process in a flow path of a microchannel structure as defined for the first aspect of the invention. This microfluidic process typically requires that there are additional functionalities/parts in the microchannel structure such as additional flow paths containing or not containing porous beds of the type required by the method of the invention. For each of at least one, two or more of the microchannel structures of a device, the method comprises the steps of:

(i) providing a first liquid aliquot containing a solute S in a position that is upstream of a porous bed II (105,205, 305) of a flow path (101,201a,a',301a,a') which comprises both porous bed II (105,205,305) and porous bed I (104,204,304), (ii) transporting the aliquot through porous bed II (105, 205,305), and (iii) transporting solute S subsequently through porous bed I (104,204,304).

Step (i) comprises that the aliquot and/or solute S is formed within the device/microchannel structure or is dispensed to the microchannel structure. Formation of the aliquot and/or of solute S is typically in a position upstream of porous bed II (105,205,305). Dispensing of the aliquot is to a position upstream of porous bed II (105,205,305) and via an inlet port of each of microchannel structures utilized in the method. This inlet port is in liquid communication with the flow path at a position that is upstream of porous bed II (105,205,305). The functionality in which formation is taking place or the inlet port to which the aliquot is dispensed may be common to several microchannel structures.

The sequence (i)-(iii) typically means that an immobilized reactant in porous bed I (104,204,304) is neutralized, for instance transformed to another group or compound that then may become available a) as an immobilized product that can be used as reactant in a subsequent step of the process, for instance a subsequent run of the sequence (i)-(iii), or b) as a product released from porous bed I (104,204,304) and used in other steps of the process.

Porous beds I and II (104,204,304;105,205,305) that comprise immobilized reactants (R and $R_{DS}$) that are non-substrate components of catalytic systems may be reusable in repetitive runs of the sequence (i)-(iii). An analytically detectable product/reactant formed as described may be used as an indicator for characteristics of the process, for instance reflecting characteristics of a solute S that is an analyte. Analytes can thus be determined from values obtained by measuring this kind of products/reactants if the process is analytical if there is an analyte to be characterized. The measurement may take place in reaction microcavity I (102,202, 302)/porous bed I (104,204,304) and/or downstream this microcavity/porous bed.

The sequence (i)-(iii) may be repeated once, twice or more as required by the process to be carried out. This means that the process and also the method may comprise a second run of steps (i)-(iii) in which a second liquid aliquot is used. This second aliquot typically contains another solute S, one or more disturbing substances that possibly are different from the disturbing substance of the first aliquot, other buffers or buffer concentrations and/or a different solvent composition, etc. The second aliquot is provided in the same flow path (301*a*) as the first aliquot or in another flow path (301*a'*) containing both porous beds I and II.

The ability of the porous bed II in this other flow path (301*a'*) to interact with disturbing substances is typically different from the corresponding ability of the porous bed II (105,205,305) in the first utilized flow path (301*a*). Still further aliquots ($3^{rd}$, $4^{th}$ etc) containing solute S and disturbing substances may subsequently be provided in subsequent repetitive runs of the sequence (i)-(iii). For each of the additional aliquots/runs ($2^{nd}$, $3^{rd}$, $4^{th}$ . . . ) porous bed II (105,205, 305) and flow path is selected to be able to hinder disturbing substances to reach porous bed I (104,204,304) simultaneously with or before solute S of the aliquot transported.

Before the first run, between runs and/or subsequent to the last run of the sequence (i)-(iii), each of one or more additional liquid aliquots may be provided a) upstream of porous bed II (105,205,305) in a flow path (101,201*a*,301*a,a'*) containing porous bed II (105,205,305), or b) upstream of porous bed I (104,204,304) in a flow path (201*b*,301*b*) not containing porous bed II (105,205,305).

These additional aliquots are typically devoid of disturbing substances including that they may contain disturbing substances that for various reasons have been considered acceptable for the process. They are typically washing or conditioning liquids lacking a solute S and possibly containing buffering substances, water, water-miscible solvents, and surface active agents such as detergents and/or tensides. One or more of them may contain a solute S.

The method and the process according to the invention may also comprise processing of liquid aliquots that do not require that the aliquots are passed through porous beds I (104,204, 304) and II (105,205,305). Typical such steps are processing downstream of porous bed I (104,204,304) and upstream of porous bed II (105,205,305).

The transport during steps (ii) and (iii) in the first and/or in a repetitive run may be selected to provide static or flow conditions for the interaction between a) the immobilized reactant $R_{DS}$, such as affinity counterpart $AC_{DS}$, and the disturbing substance, and/or b) immobilized reactant R, e.g. affinity counterpart $AC_S$, and solute S.

Typical flow rates through a porous bed for flow conditions provide a residence time $\geq 0.010$ seconds such as $\geq 0.050$ sec or $\geq 0.1$ sec with an upper limit that typically is below 2 hours such as below 1 hour. Illustrative flow rates are within 0.01-1000 nl/sec, such as 0.01-100 nl/sec and more typically 0.1-10 nl/sec. These flow rate intervals may be useful for bed volumes in the range of 1-200 nl, such as 1-50 nl or 1-25 nl. Residence time refers to the time it takes for a liquid aliquot to be in contact with the solid phase in the reaction microcavity. The flow rate may be adapted such that the interactions referred to are taking place under diffusion-limiting or non-diffusion limiting conditions. Further details and advantages with flow conditions are given in WO 0275312 (Gyros AB).

The sequence (i)-(iii) may be part of (a) separation method, (b) a method of catalysis, (c) a solid phase synthesis etc.

Separation comprises among others:

a) capturing, i.e. porous bed I exhibits an affinity structure (affinity ligand, affinity reactant) with binding ability for a solute S such that when a liquid containing solute S passes through the bed then a liquid without solute S or with a reduced amount of solute S will appear in the eluate, and/or b) immobilization of the solute on the solid phase material for later use of the solid phase material so modified in capturing, catalytic reactions, solid phase synthesis etc.

For alternative (a) (capturing), the solute becomes bound to porous bed I (104,204,304) and forms an immobilized affinity complex comprising the affinity structure and the solute.

For immobilization (alternative b), porous bed I (104,204, 304) may exhibit a generic affinity structure L' (generic ligand) ($=AC_S$) that is an affinity counterpart to a conjugate B'-$AC'_S$ ($=S'$) which has two kinds of binding sites—the first one B' is generic and directed towards generic affinity structure L' on porous bed I (104,204,304) and the second one $AC'_S$ towards a solute S. L', B', S' and $AC'_S$ then correspond to L, B, S and $AC_S$ above and what has been said in the context of the first aspect of the invention for L, B, S and $AC_S$ including affinity constants also applies here.

A separation may be part of a purification or an enrichment protocol for solute S. Solute S may be a contaminant or the entity to be purified, enriched etc. The separation may also be part of a synthetic protocol, preparative protocol, a cell based assay, various kinds of affinity assays including nucleic acid assays, immunoassays, enzyme assays and other ligand-receptor assays based on the affinity between a receptor and a ligand.

An affinity assay that utilizes a capturing step for binding solute S to a reactant R immobilized on a solid phase material (porous bed I (104,204,304)) typically aims at the characterization of an uncharacterized feature or variable of a reactant (=analyte) utilized in the assay. Typical features/variables are of two kinds: a) amounts including presence and/or absence, concentration, relative amounts, activity such as binding activity and enzyme activity, etc, and b) properties of affinity reactants including affinity as such, e.g. affinity constants, specificities etc. Reaction variables such as pH, temperature, ionic strength etc and their influence on the outcome of the experiments/reactions at issue may also be characterized/determined (yield, precision, recovery etc). See WO 02705312 (Gyros AB).

Two major groups of affinity assays to which the present invention can be applied are a) competitive affinity assays including also inhibition and displacement assays, or b) non-competitive affinity assays including sandwich assays. The conditions in an affinity assay are selected so that the amount of the affinity complex is correlated with the absence, the presence and/or the amount (including concentration) of an analyte in a sample. An affinity assay may be heterogeneous in the sense that it in at least one step utilizes an affinity reaction between an immobilized reactant and an affinity counterpart in order to form an affinity complex. An affinity assay may utilize an analytically detectable reactant to measure an affinity complex, the amount of which correlates with the absence, the presence and/or the amount of an analyte in a sample. An analytically detectable reactant used in an affinity assay may be inherently detectable or be a man-made conjugate between an affinity reactant and a label compound. There are two major kinds of labels:

a) signal-emitting labels such as enzymatic labels (enzyme, coenzyme, substrate, cosubstrate, cofactor et), radioactive isoptopes, chromophors and/or chromogens, fluorophors and/or fluorogens, bioluminophors and/or bioluminogens, chemiluminophlors and/or chemiluminogens, metal atoms and ions, etc, and b) affinity labels that typically require secondary detectable reactants comprising one part that is capable of binding to an affinity label and a another part that is analytically detectable.

A catalytic reaction as applied to the present invention comprises that the solid phase material (porous bed I (104, 204,304)) exhibits one or more immobilized components (affinity structure, affinity ligand, affinity reactant) of the catalytic system utilized, while one of the other components of the same system is solute S. The catalytic reaction comprises formation of an affinity complex between the immobilized member (affinity structure, affinity ligand, affinity reactant) and solute S plus possibly also other members of the catalytic system.

The term "catalytic system" includes single catalytic system and more complex variants comprising a series of linked single enzyme systems, single catalytic systems linked to other reaction systems, whole cells, cell parts exhibiting enzymatic activity etc. The bed may function as a catalytic reactor, such as an enzyme reactor. Enzyme receptor-ligand assays (enzyme affinity assays), such as enzyme immunoassays are examples of processes that utilizes linked catalytic systems, e.g. linked to other receptor-ligand reactions.

The step during which interaction between the immobilized reactant R and solute S occurs may be part of a catalytic assay, such as an enzyme assay, for characterizing one or more members of the catalytic system or some other reaction variable (e.g. reaction condition). The assay may be for determining the activity of a particular catalyst, substrate, cosubstrate, cofactor, co-catalyst etc in a liquid sample. The term catalytic assay also contemplates so called enzyme immuno assays. The molecular entity/entities corresponding to the activity to be determined is/are called analyte/analytes. See WO 03093802 (Gyros AB).

Solid phase synthesis includes for instance polymer synthesis, such as oligopeptide and oligonucleotide synthesis and synthesis of other small molecules on a solid phase material. The immobilized reactant used in polymer synthesis, for instance, may exhibit the structure of the corresponding monomer, such as nucleotide, carbohydrate, amino acid structure, and mimetics of these structures. Synthesis of libraries of immobilized members of combinatorial libraries is also included. Such members have relatively low molecular weights (e.g. <10,000 dalton including a possible spacer to a polymeric backbone).

Microfluidic Devices Comprising Generic Ligands

The third aspect of the invention comprises a microfluidic device in which there are one, two or more microchannel structures. At least one of these microchannel structures comprises one, two or more flow paths (101,201a,a',301a,a',b) and each of at least one, two or more of these flow paths (101,201a,a',301a,a') comprises two porous beds (104,204, 304;105,205,305) in series as described for the first aspect. As for the first aspect there may be additional functional units upstream of the upstream porous bed (105,205,305), between the porous beds (104,204,304;105,205,305), and downstream of the downstream porous bed (104,204,304).

The characteristic feature is that in each flow path that comprises the upstream porous bed and the downstream porous bed, at least one, preferably both, of the beds comprises/comprise a generic ligand L that may be the same or different in the two beds. This ligand is in each bed immobilized to the solid phase material of the bed. The two ligands in a flow path are represented with $L_I$ for the downstream bed (104,204,304) and $L_{II}$ for the upstream bed (105,205,305). In the case there are two or more flow paths comprising the two porous beds the combination of generic ligands may be different between at least two of the flow paths, but preferably the combination is the same in all flow paths containing porous bed I and porous bed II.

Typical combinations of ligands in a flow path comprising bed I and bed II are: 1) $L_I=L_{II}$, 2) $L_{II}$=anti-$L_I$, and 3) $L_I$=anti-$L_{II}$. For biotin and biotin-binding compounds (=anti-biotins) as generic immobilizing affinity pair this means: 1) $biotin_I$; $biotin_{II}$ or $anti_I$-biotin;anti-$biotin_{II}$, 2) $biotin_I$;anti-$biotin_{II}$, and 3) anti-$biotin_I$;$biotin_{II}$.

The binding capacity of porous bed I or II (104,204,304; 105,205,305) for a generic ligand L can be measured as the amount of ligand in mole per unit volume, disregard blocking and destruction of binding sites caused by the immobilization. With this measure suitable binding capacities will typically be found within the interval of 0.001-3000 pmole, such as 0.01-300 pmole, per nl solid phase in bed form saturated with liquid. For instance, if 0.1 pmole streptavidin per nl has been immobilized this corresponds 0.4 pmole/nl biotin-binding sites. The conversion factor four is because streptavidin has four binding sites for biotin per streptavidin molecule. Binding capacity can also be measured as actual binding capacity for binder B, i.e. mole active binding sites per unit volume of the solid phase containing the immobilized affinity ligand in bed form saturated with liquid. This kind of binding capacity will depend on the immobilization technique, the pore sizes of the solid phase, the size of the entity to be immobilized, the material and design of the solid phase etc. Ideally the same ranges apply for the actual binding capacity as for the total amount of binding sites (as defined above). The actual binding capacity primarily refers to binding/capturing of the binder B in its basic form, e.g. unconjugated and/or underivatized. See also WO 04083109 (Gyros AB).

Other characteristic features of the third aspect of the invention with respect to microchannel structures/microfluidic devices including various flow paths, microcavities, functional units etc, solid phase material etc may be as discussed for the third aspect of the invention.

EXPERIMENTAL PART

Experiment 1

Combination of a Dummy Porous Bed with a Porous Bed Exposing Anti-Analyte Antibody Compared to a Sole Porous Bed Exposing Anti-Analyte Antibody This example describe a sandwich immunoassay for PDGF β-receptor in cell lysates from porcine aorta endothelial (PAE) cells stably expressing the membrane bound PDGF β-receptor and stimulated with +/− ligand PDGF-BB. The capture antibody was raised against the target protein and the detection antibody against a regulatory phosphorylated amino acid site. The assay including immobilization, labeling (Alexa 647) and microchannel structure/microfluidic device/ instrument is the same as for the myoglobin assay in WO 04083108 (Gyros AB). The microchannel structure used is given in FIG. 1 of WO 04083108. The porous bed was placed in reaction microcavity (104).

Cell culture: PAE cells were transfected with PDGF β-receptor and one of the cell cultures were also G-418 selected [Claesson-Welsh, L. et al. *cDNA cloning and expression of a human platelet-derived growth factor receptor specific for B-chain containing PDGF molecules*. Mol. Cell. Biol. 8 (1988) 3476-3486]. The cells were grown in Ham's F-12 medium supplemented with 10% fetal calf serum, 100 µg/ml streptomycin and glutamine. A nearly confluent monolayer of cells were starved overnight in Ham's F-12 supplemented with 0.1 mg/ml bovine serum albumin (BSA) and +/− stimulated with 100 ng/ml PDGF-BB for 60 minutes on a shake plater. Unstimulated cells are used as a control since the cells only have unphosphorylated PDGF β-receptors. The receptors are activated and saturated with high concentration of ligand inhibiting internalisation followed by degradation during the stimulation. After the stimulation, cells were washed twice in ice-cold PBS buffer and scraped off with a "rubber police men" in 1 ml PBS. The cell suspension were saved and lysed in 200 µl ice-cold lysis buffer (20 mM Tris-HCl pH 7.5, 150 mM NaCl, 10 mM EDTA, 0.5% Triton X-100, 0.5% Deoxycholate, 0.5 mM $Na_3VO_4$ and 1% Trasylol (Bayer) for 15 min on ice. The lysates were centrifuged at 13000 rpm for 15 min at 4° C. and the supernatant were saved in aliquots and stored at −20° C. The cells were in a first grown in 75 $cm^2$ culture dishes and in a second run in 175 $cm^2$ culture flasks in order to make more concentrated lysates. Total protein was quantitated according to BCA Protein Assay Kit Microplate procedure from PIERCE Biotechnology (Boule Nordic AB, Huddinge, S.).

PDGF β-receptor antibodies: Rabbit polyclonal antibody 958 raised against a recombinant protein corresponding to amino acids 958-1106 of the carboxy terminus of human PDGF β-receptor, goat polyclonal antibody P-20 raised against a peptide of the carboxy terminal of human PDGF β-receptor, and mouse monoclonal PY99 were from Santa Cruz Biotechnologies (Santa Cruz, Calif.). The PDGF β-receptor antibodies P-20 and 958 are recommended for the detection of PDGF receptor type β of human and, to a lesser extent, of mouse and rat origin by western blotting, immunoprecipitation and immunohistochemistry. They should not be cross-reactive with PDGF receptor type α. The antibodies have been used extensively in immunoprecipitation and Western Blot experiments with the same cell culture [Pietras K., et al. Inhibition of PDGF Receptor Signaling in Tumor Stroma Enhances Antitumor Effect of Chemotherapy. Cancer Research 62 (2002) 5476-5480].

Sandwich-based immunoassay methods: In the assay, wash buffers and antibodies were distributed through the common distribution channel and cell lysate preparations through the individual inlets. Every batch run included standards in triplicates and blank samples. The assay included a small dilution series (+/−PDGF-BB) and several blanks with lysis buffer. All steps in the assay were automatically run in the Gyrolab Workstation (Gyros AB).

In the assay different combinations of antibodies were tested to find the combination giving the highest degree of specific binding, 958/PY99, 958/P-20, P-20/P-20, P-20/958 and P-20/PY99 (capturing/detecting).

Titration showed that the concentration of the detection antibody should be 400 nM.

The β-PAE cell lysate with +/−PDGF-BB stimulation was diluted in lysis buffer (2×, 4×, 8×). Undiluted cell lysate was included as a standard point.

Immobilization of capture antibody: The porous beds were washed twice with PBS-T (0.015 M Na—$PO_4$ pH 7.4, 0.15 M NaCl, 0.01% $NaN_3$, 0.01% Tween-20) followed by a short spin to recondition the polystyrene beads coated with phenyldextran to which streptavidin has been immobilized. Biotinylated capture antibody diluted in the wash buffer was added at a concentration of 667 nM followed by a spin. Washing was repeated twice in the same manner as the reconditioning.

Basic assay protocol: The cell lysate was added to individual inlets, volume defined (200 nl) and transported into the porous beds where PDGF β-receptor (analyte) was captured. After two wash steps followed by a short spin to ensure that the beds were filled with liquid during the fluorescence detection. The background fluorescence detection included three detection steps with different sensitivity set on the LIF detector, 1%, 5% and 25%. Excess buffer was washed away by a short spin before addition of the detection antibody which was allowed to bind to the analyte during a spin step. Six wash steps were finally included, two with normal wash buffer and four with wash buffer containing isopropanol 20%, to remove excess detection antibody.

In the beginning, cell lysate runs were mainly performed according to the basic assay protocol with the capture antibody being distributed all over the porous bed. Modifications were tested because of difficulties to establish a specific interaction between the PDGFβ-receptor and the antibodies. First of all, the analyte and the detection antibody spin program were extended and the linear flow over the bed reduced to enable the PDGF β-receptor in the cell lysate to attach to the capture antibody. After addition of analyte, three extra wash steps were included with PBS buffer without Tween-20 and the second and the fourth wash step were followed by a pulsed spin program, allowing the solution to move through the beds by simple diffusion. The final wash steps after the detection antibody were the same as in the preceding paragraph with the exception that isopropanol was excluded in the wash buffer.

Due to uncontrolled non-specific interactions in the cell lysate assay a second porous bed (II) devoid of capture anti-analyte antibody was loaded on top of the porous bed (I) exposing anti-analyte antibody. Porous bed (II) consisted of the gel filtration media Superdex™ peptide (Amersham Biosciences, Uppsala, Sweden). It media was loaded in a 5× dilution slurry onto porous bed I (polystyrene beads coated with phenyldextran to which streptavidin has been immobilized). Superdex™ peptide is used for high-resolution gel filtration of peptides and other small biomolecules of 100-7000 daltons in molecular weight.

Results

From pre-experiments three antibody pairs were selected P-20/958, P-20/PY99 and 958/PY99.

Porous bed (I) solely. The cell lysate experiments resulted in high CV values due to the signal distribution (triplicates) in the bed. In some experiments a small difference in signal could be seen between undiluted cell lysate and blank signals but mostly significant signals were hard to distinguish from background signals. The enrichment in the beds was mostly irregular and a general bed pattern could not be seen, in some cases the signal had a tendency to progress down the porous bed.

Porous bed (II) upstream of porous bed (I). Two combinations were tested:
a) a bed of polystyrene beads (essentially non-porous) coated with phenyldextran on top of a bed of polystyrene particles coated with phenyldextran to which streptavidin has been immobilized, and b) a bed of Superdex™ peptide on top of a bed of polystyrene beads coated with phenyldextran to which streptavidin has been immobilized.

The Superdex™ peptide combination showed improvement in responses for the three antibody pairs compared to the single bed variant. Differences between cell lysate and blank responses could also be discerned.

Experiment 2

Neutralization of Effects of Heterophilic Antibodies in Native Samples

Basic assay: The microfluidic sandwich fluorescence immunoassay for TNFα was as outlined for myoglobin in the experimental part of WO 04083108 (Gyros AB). The solid phase and the immobilization technique and the fluorescence labelling technique were also as outlined WO 04083108 (Gyros AB). The assay was modified by placing an IgG-bed or the corresponding bed devoid of immobilized IgG (in control experiments) immediately upstream of the bed exposing capture anti-TNFα mouse antibody.

Instrument and microfluidic device: Both were the same as used in WO 04083108 (Gyros AB).

Samples: Three human serum samples rich in heterophilic antibodies and one normal were used in A. All four samples were spiked with human TNFα (200 pg/ml) and used in B.

Solid phase—Immunglobulin: The same kind of streptavidin particles as used in WO 04083108 (Gyros AB) were in a batch mode coated with four combinations of bovine IgG och mouse IgG—bovine IgG:mouse IgG 10:1; bovine IgG:mouse IgG 1:1; bovine IgG; mouse IgG. The particles were then loaded on top of a bed exposing capture anti-TNFα mouse antibody. The loading technique for both beds was the same as outlined for the anti-myoglobin antibody bed in WO 04083108 (Gyros AB). The flow direction during the experiment is from the IgG-bed to the anti-TNFα mouse antibody bed.

Experiments: Effects of an IgG-bed in front of the anti-TNFα mouse antibody bed on A) assaying heterophilic antibodies in four human serum samples given above, B) Recovery of TNFα for the TNFα assay of TNFα spiked human serum samples given above, and C) standard curve.

Figure 4:
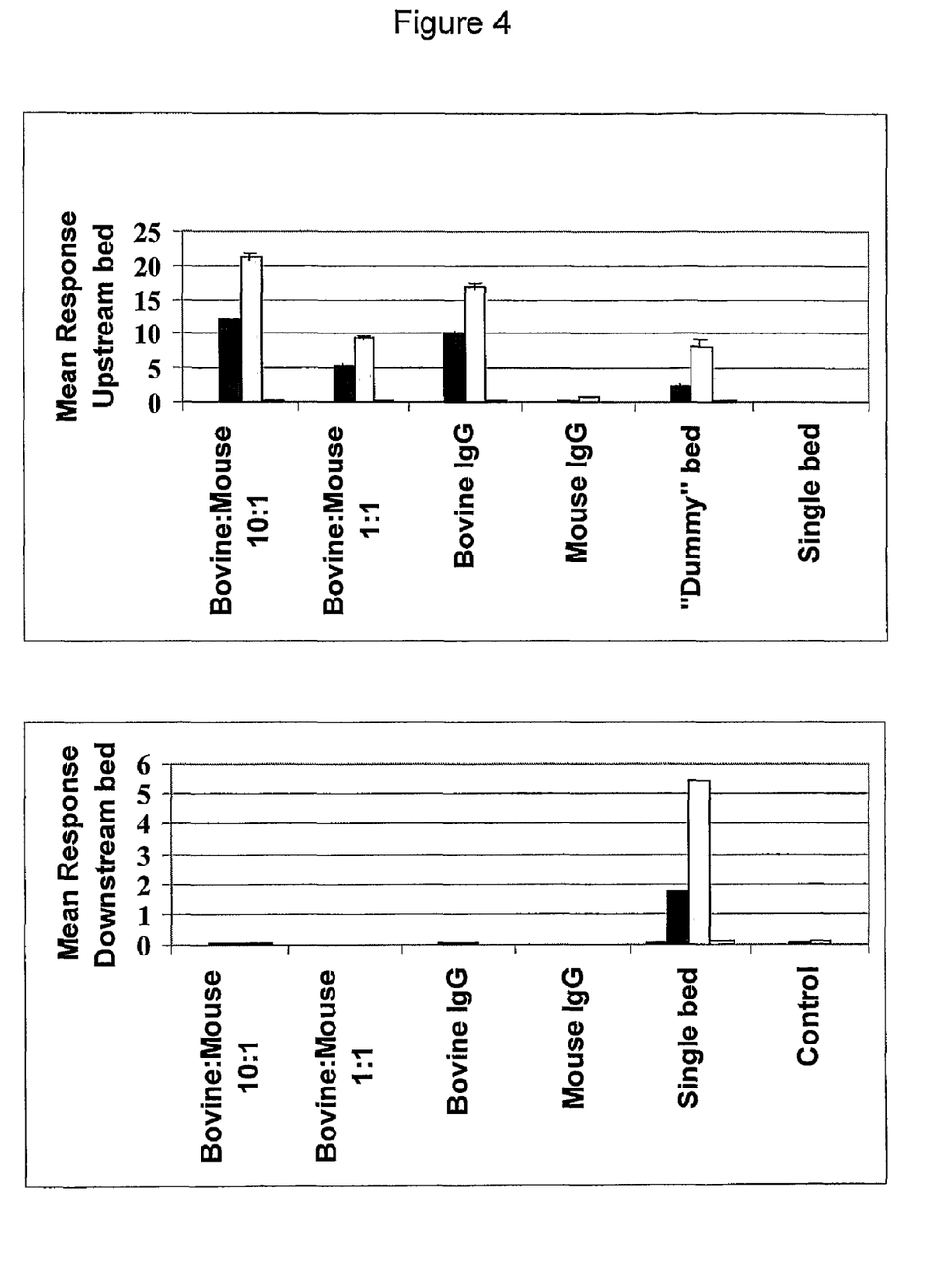
FIG. 4 illustrates results of experiment 2A.

Results of (A): See FIG. 4. The staples in each group represent individual samples. It is apparent that the IgG-bed based on a bovine:mouse IgG of 10:1 was most efficient in capturing heterophilic antibodies. No heterophilic antibodies were detected in the normal serum sample. Without the use of an IgG-bed in front of the anti-TNFα mouse antibody bed the latter bed captured large amounts of heterophilic antibodies that would disturb a TNFα assay based on the anti-TNFα mouse antibody bed.

Figure 5A:
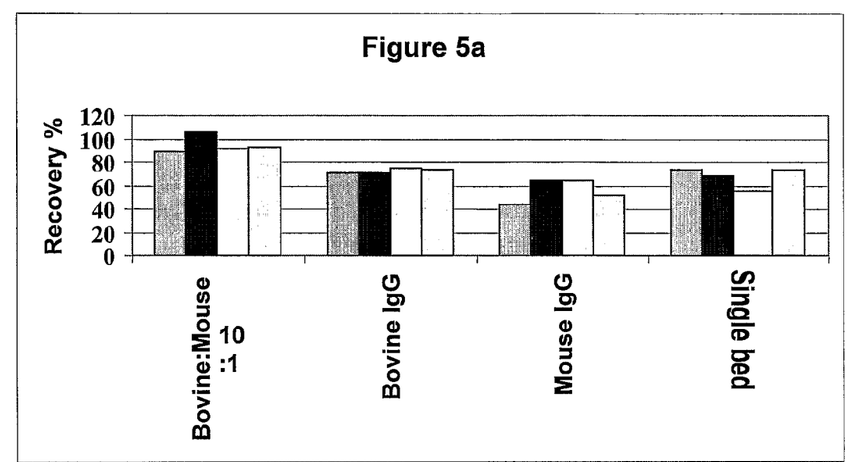
FIGS. 5a-b illustrate results of experiment 2B

Results of (B): See FIG. 5*a*. The staples in each group represent individual samples, again with no staples for the normal serum sample. The change in recovery of TNFα when placing an IgG-bed in front of the anti-TNFα mouse antibody bed was acceptable.

Figure 5B:
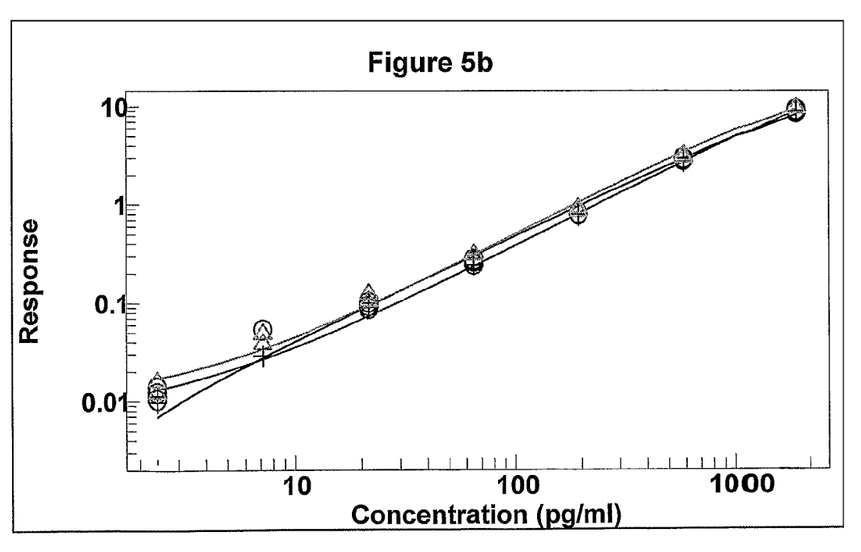

Results of (C): See FIG. 5*b*. The change of the standard curve was insignificant when placing different IgG-bed in front of the anti-TNFα mouse antibody bed compared to without an IgG-bed.

Certain innovative aspects of the invention are defined in more detail in the appending claims. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A microfluidic device comprising a microchannel structure in which there are two or more flow paths all of which comprises a porous bed I that is common for all of the flow paths and is provided in a detection microcavity permitting measurement on the porous bed, which bed exposes an immobilized reactant R that is capable of interacting with a solute S that passes through the bed, wherein at least one of the flow paths comprises a second porous bed II that is placed upstream of porous bed I and is dummy with respect to interaction with solute S but capable of interacting with a substance DS that is present in a liquid aliquot together with solute S and is capable of disturbing the result of the interaction between solute S and said immobilized reactant R.

2. The microfluidic device of claim 1, wherein porous bed I and porous bed II are physically separated from each other.

3. The microfluidic device of claim 1, wherein at least one of porous bed I and porous bed II bed is a packed bed of particles and the remaining porous bed, if any, is a porous monolithic plug.

4. The microfluidic device of claim 1, wherein at least one of porous bed I and porous bed II comprises a solid phase material that is a size exclusion material.

5. The microfluidic device of claim 1, wherein the disturbing substance is smaller than solute S and that at least porous bed II in at least one of said flow paths comprises a solid phase material that is a size exclusion material having an exclusion limit delaying the disturbing substance from passing through porous bed II in relation to solutes.

6. The microfluidic device of claim 1, wherein at least one, two or more of the remaining ones of said two or more flow paths is/are devoid of porous bed II.

7. The microfluidic device of claim 1, wherein the porous bed II in said two or more flow paths comprise an immobilised reagent $R_{DS}$ that is capable of interacting with the disturbing substance that is present together with a solute.

8. The microfluidic device of claim 7, wherein the $R_{DS}$ in at least one of said two or more flow paths differs from $R_{DS}$ in at least one of the remaining ones of said two flow paths.

9. A microfluidic process carried out in a flow path of a microchannel structure of a microfluidic device of claim 1, said process comprising transporting a liquid aliquot containing a solute S through a porous bed I that is placed in said flow path and exhibits an immobilized reactant R that is capable of interacting with solute S during the transport, characterized in comprising the steps of (i) providing said flow path in a form that comprises a porous bed II that is upstream of porous bed I and dummy with respect to interaction with solute S but capable of interacting with a disturbing substance DS, (ii) providing a liquid aliquot containing said solute S and said disturbing substance in said flow path in a position that is upstream of porous bed II, (iii) transporting the aliquot through porous bed II,
(iv) transporting subsequently solute S through porous bed I to allow for the interaction with reactant R, and
(v) detecting interacted solute S in the porous bed I by measurement on the porous bed.

10. A microfluidic device comprising a microchannel structure that comprises two or more flow paths each of which comprises a porous bed I that is common for all of said flow paths and at least one of which comprises a porous bed II which is upstream of porous bed I, wherein porous bed I is provided in a detection microcavity permitting measurement on the porous bed, wherein both of porous bed I and porous bed II in said two or more flow paths comprises a solid phase material containing a generic ligand, and which further comprises a liquid router in the flow path between porous beds I and II, wherein the liquid router is connected to an exit microconduit.

11. The microfluidic device of claim 10, wherein the generic ligand in porous bed II in one or more of said at least one flow path are the same as in porous bed I.

12. The microfluidic device of claim 10, wherein the generic ligand in porous bed II in one or more of said flow paths is an affinity counterpart (anti-ligand) to the generic ligand in porous bed I.

13. The microfluidic device of claim 10, wherein said generic ligand is biotin or anti-biotins.

14. The microfluidic device of claim 1, further comprising a liquid router in the flow path between porous beds I and II and which is connected to an exit microconduit.

* * * * *